United States Patent [19]
McMinn

[11] Patent Number: 4,501,029
[45] Date of Patent: Feb. 26, 1985

[54] TENDON REPAIR

[76] Inventor: Derek J. W. McMinn, 26 Chesterwood Rd., Kings Heath, Birmingham 13, England

[21] Appl. No.: 484,606

[22] Filed: Apr. 13, 1983

[30] Foreign Application Priority Data

Apr. 22, 1982 [GB] United Kingdom ............... 8211608

[51] Int. Cl.³ .................. A61F 1/24; A61F 1/00; A61B 17/04
[52] U.S. Cl. ........................................ 3/1; 128/334 R
[58] Field of Search ................ 3/1, 1 B; 128/334 R, 128/334 C, 1 R

[56] References Cited

U.S. PATENT DOCUMENTS

| 3,463,158 | 8/1969 | Schmitt et al. | 3/1 |
| 3,577,837 | 5/1971 | Bader | 3/1 |
| 3,786,817 | 1/1974 | Palma | 128/334 R |
| 3,797,047 | 3/1974 | Pillet | 3/1 |
| 3,833,002 | 9/1974 | Palma | 128/334 R |
| 3,842,441 | 10/1974 | Kaiser | 3/1 |
| 3,938,528 | 2/1976 | Bucalo | 128/334 C |

Primary Examiner—Ronald L. Frinks
Attorney, Agent, or Firm—Staas & Halsey

[57] ABSTRACT

A device for assisting in repair of a severed tendon comprises a main tube for insertion between a replacement tendon and its sheath, and a plurality of passages extending transversely of the bore of the main tube and communicating therewith, through which passages a blood supply from the sheath to the replacement tendon is established. The lengths of the passages are such that free movement between the tendon and its sheath is permitted after the blood supply is established.

7 Claims, 5 Drawing Figures

TENDON REPAIR

This invention relates to a device for assisting in the repair of severed tendons.

It is usual to effect repair of a severed tendon by threading a replacement tendon through the tendon sheath and securing the ends of the replacement tendon to undamaged parts of the original tendon. Blood supply to a tendon is by way of fine blood vessels, or viniculae which extend between the tendon and its sheath and are of sufficient length as to enable the required movement of the tendon within the sheath, this movement being as much as 35 mm in the tendons of the hand. However, the blood supply to a replacement tendon tends to be re-established by the shortest routes between the tendon and sheath, and the fibrous tissue surrounding the re-established blood vessels serves to prevent movement of the tendon, and hence of the member which it controls. It is therefore common practice to perform a second operation to sever those fibrous tissues to restore some mobility to the member.

The foregoing procedures frequently result in some permanent impairment of mobility. Such impairment is particularly disadvantageous when tendons have been severed in the hand or the wrist, which is a common form of industrial accident.

It is an object of the present invention to provide a device which, when used in the repair of severed tendons will permit re-establishment of blood supply to the tendons, without the foregoing disadvantages.

According to the invention, a device for assisting in repair of a severed tendon comprises a main tube for insertion between a replacement tendon and its sheath, and a plurality of transversely extending passages which communicate with the bore of said main tube at intervals over substantially the whole length thereof, the lengths of said passages being at least equal to the minimum required lengths of blood vessels between the tendon and its sheath which will permit free movement of the tendon within the sheath.

Embodiments of the invention will now be described by way of example only, and with reference to the accompanying drawings in which.

Figure 1:
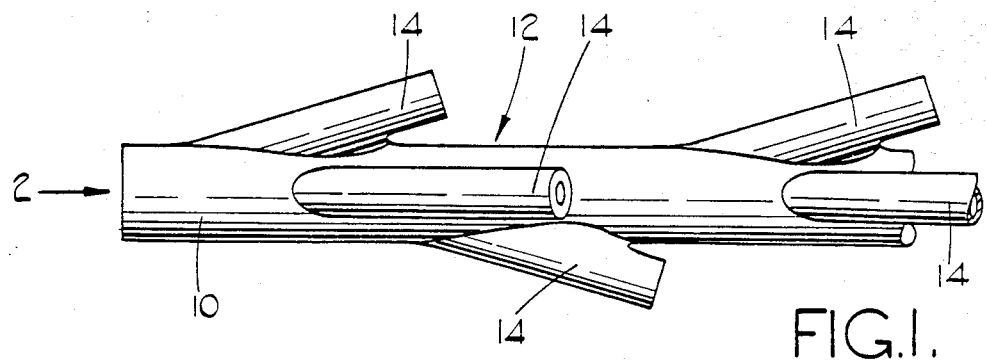
FIG. 1 is an external view of part of a device according to the invention.
Figure 2:
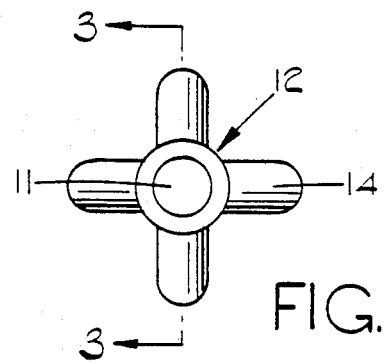
FIG. 2 is a view on arrow 2 in FIG. 1.
Figure 3:
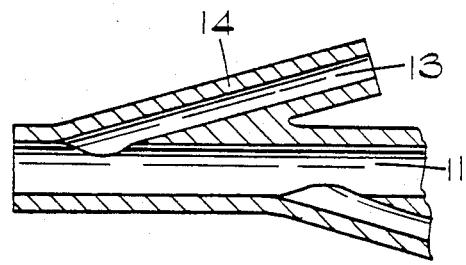
FIG. 3 is a section on line 3—3 in FIG. 2.

As shown in FIGS. 1 to 3, a tube 10 is intended to assist in repair of a tendon of the hand. The tube 10 has an overall length of 20 cm, an axial bore 11 having a diameter of 4 mm and an outer circumference 12 having a diameter of 7 mm. Communicating with the bore 11 and extending transversely thereof are a plurality of passages 13 which are housed in projections 14 from the main body of the tube 10 and moulded integrally therewith. Each of the passages 13 and its surrounding projection 14 is at an angle of 15° to the bore 11, and all of the projections 14 are directed towards one end of the tube 10. The passages 13 have bores of 2 mm diameter and the projections 14 have outside diameters of 4 mm. The minimum length of each of the passages 13 is equal to at least half the anticipated distance of movement of the tendon to be repaired, and is typically at least 20 mm. The passages 13 are evenly spaced along the length of the tube 10 at intervals of 10 mm. Conveniently, the passages 13 and their surrounding projections 14 are angularly spaced about the axis of the bore 11, but it will readily be understood that they could, if desired, be located on alternate opposite sides of the tube 10, or in any other arrangement which might be convenient for the particular use to which they are to be put.

The tube 10 is formed of a synthetic material which is absorbable within the human body. Such a material is polyglycolic acid which, in contact with the body breaks down to its amino acid components, these being subsequently metabolised.

Figure 4:
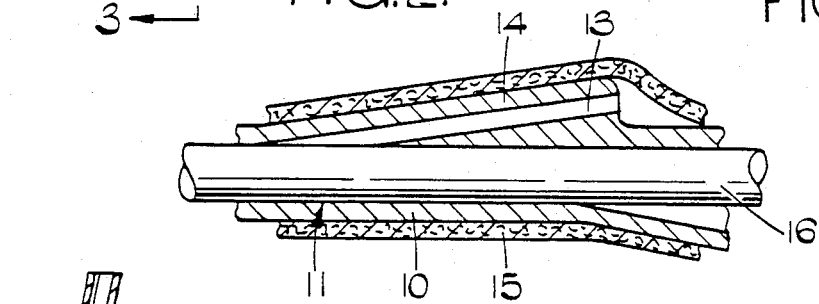
FIG. 4 is a longitudinal section of an alternative form of device, in position between a tendon and its sheath.

The alternative embodiment shown in FIG. 4 has the passages 13 at an angle of 10° with the axis of the bore 11. In this embodiment the projections 14 extend for a less distance radially of the bore 11 and are, in fact, integral with the remainder of the tube 10 over the whole of their length.

For use of either of the foregoing embodiments the tube 10 is inserted in a tendon sheath 15 (FIG. 4) and the replacement tendon 16 is threaded through the bore 11 and its opposite end secured to adjacent ends of the undamaged part of the original tendon. Blood supply to the replacement tendon from its sheath is established through the passages 13. However, the fibrous tissue surrounding the new blood vessels has a length equivalent to that of the passages 13, and subsequent breakdown of the tube 10 permits the replacement tendon to move freely within its sheath.

Figure 5:
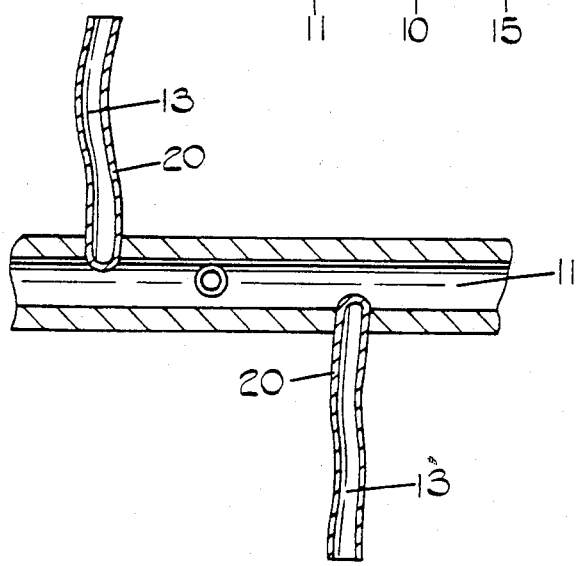
FIG. 5 is a section, corresponding to FIG. 3, of a further alternative form of the device.

In the further embodiment shown in FIG. 5 the tube is of an elastomeric flexible material which is not absorbable in the body, for example a silicone rubber of the type marketed by Dow Corning under the name SILASTIC. In this embodiment the passages 13 are provided within thin-walled silicone rubber tubes 20 which extend transversely of the bore 11 and are secured to the wall thereof. As before, the passages have bores of 2 mm and lengths equal to at least half the anticipated movement of the replacement tendon in its sheath, these length typically being at least 20 mm.

In use, this last embodiment is located, as before, between a replacement tendon and its sheath, and blood supply to the replacement tendon is established through the passages 13. The device is, however, allowed to remain in place within the tendon sheath, the thin-walled tubes 20 flexing with movement of the tendon.

Each of the described embodiments permits re-establishment of blood supply to a replacement tendon, along paths whose lengths correspond to those of viniculae associated with an undamaged tendon.

I claim:

1. A device for assisting in repair of a severed tendon, comprising a main tube for insertion between a replacement tendon and its sheath, and a plurality of transversely extending passages which communicate with the bore of said main tube at intervals over substantially the whole length thereof, the lengths of said passages being at least equal to the minimum required lengths of blood vessels between the tendon and its sheath which will permit free movement of the tendon within the sheath.

2. A device as claimed in claim 1 in which said tube is of a synthetic material which is absorbable in the body.

3. A device as claimed in claim 2 in which said transversely-extending passages are moulded integrally with the remainder of said device.

4. A device as claimed in claim 1 in which said transversely-extending passages are provided within thin-walled flexible tubes.

5. A device as claimed in claim 4 in which said main tube and said thin-walled tubes are of an elastomeric material.

6. A method of repairing a severed tendon, including the steps of inserting into the sheath of the tendon a device comprising a main tube of flexible material and a plurality of transversely extending passages which communicate with the bore of said main tube at intervals over substantially the whole length thereof, the lengths of said passages being at least equal to the minimum required lengths of blood vessels between the tendon and its sheath which will permit free movement of the tendon within its sheath, inserting said replacement tendon through the bore of said main tube, and securing the ends of said replacement tendon to undamaged parts of the original tendon.

7. A method as claimed in claim 6 in which said device remains within said tendon sheath.

* * * * *